(12) United States Patent
Westergaard et al.

(10) Patent No.: US 11,122,375 B2
(45) Date of Patent: *Sep. 14, 2021

(54) SYSTEM AND METHOD FOR PERSONALIZING A HEARING AID

(71) Applicant: Widex A/S, Lynge (DK)

(72) Inventors: Anders Westergaard, Herlev (DK); Niels Erik Boelskift Maretti, Birkerod (DK)

(73) Assignee: Widex A/S, Lynge (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/880,423

(22) Filed: May 21, 2020

(65) Prior Publication Data

US 2020/0280810 A1    Sep. 3, 2020

Related U.S. Application Data

(63) Continuation of application No. 15/752,479, filed as application No. PCT/EP2015/068762 on Aug. 14, 2015, now Pat. No. 10,667,062.

(51) Int. Cl.
*H04R 25/00*      (2006.01)
*G16H 40/67*      (2018.01)

(52) U.S. Cl.
CPC .......... *H04R 25/505* (2013.01); *G16H 40/67* (2018.01); *H04R 25/30* (2013.01); *H04R 25/554* (2013.01);
(Continued)

(58) Field of Classification Search
CPC .... H04R 25/505; H04R 25/30; H04R 25/554; H04R 25/558; H04R 2225/43; G16H 40/67
(Continued)

(56) References Cited

U.S. PATENT DOCUMENTS

| 6,658,307 B1 | 12/2003 | Mueller |
| 8,005,232 B2 | 8/2011 | Roeck et al. |

(Continued)

FOREIGN PATENT DOCUMENTS

| EP | 1 252 799 A0 | 7/2001 |
| EP | 1 628 503 A2 | 2/2006 |

(Continued)

OTHER PUBLICATIONS

International Search Report of PCT/EP2015/068762 dated Apr. 4, 2016.

(Continued)

*Primary Examiner* — Sean H Nguyen
(74) *Attorney, Agent, or Firm* — Sughrue Mion, PLLC

(57) ABSTRACT

A method of personalizing at least one hearing aid for a hearing aid user including manufacturing at least one hearing aid (1), receiving an audiogram from a server (37) for the hearing aid user, programming the at least one hearing aid (1) by the audiogram, whereby the at least one hearing aid (1) becomes personalized for the hearing aid user. The at least one personalized hearing aid (1) is delivered to the hearing aid user. Once the user has received the at least one personalized hearing aid (1), he may take the hearing aids into use. If there arises a need for fine tuning, the hearing aid user may request a consultation with a hearing healthcare professional. The hearing healthcare professional has equipment (44, 45) for fine tuning the hearing aid (1), and he may fine tuning the at least one personalized hearing aid (1) in dialogue with the hearing aid user. Also provided is a hearing aid delivering system and an Internet enabled personal communication device.

19 Claims, 7 Drawing Sheets

(52) U.S. Cl.
CPC ........... *H04R 25/558* (2013.01); *H04R 25/70* (2013.01); *H04R 2225/43* (2013.01); *H04R 2225/55* (2013.01)

(58) Field of Classification Search
USPC .......................................................... 381/314
See application file for complete search history.

(56) References Cited

U.S. PATENT DOCUMENTS

| | | |
|---|---|---|
| 8,064,609 B2 | 11/2011 | Baechler et al. |
| 8,112,166 B2 | 2/2012 | Pavlovic et al. |
| 8,166,312 B2 | 4/2012 | Waldmann |
| 8,302,159 B2 | 10/2012 | Griesdorf et al. |
| 8,542,842 B2 | 9/2013 | Zaccaria |
| 2002/0054689 A1 | 5/2002 | Zhang et al. |
| 2002/0066094 A1 | 5/2002 | Futakuchi |
| 2005/0283263 A1 | 12/2005 | Eaton et al. |
| 2007/0255435 A1 | 11/2007 | Cohen et al. |
| 2009/0047994 A1 | 2/2009 | Sommer |
| 2010/0067711 A1 | 3/2010 | Waldmann |
| 2010/0330909 A1 | 12/2010 | Maddern |
| 2011/0072507 A1 | 3/2011 | Johnston, II et al. |
| 2011/0082520 A1 | 4/2011 | McElveen, Jr. |
| 2011/0176686 A1 | 7/2011 | Zaccaria |
| 2011/0257994 A1 | 10/2011 | Givens et al. |
| 2012/0051569 A1 | 3/2012 | Blamey et al. |
| 2012/0183164 A1 | 7/2012 | Foo et al. |
| 2012/0183165 A1 | 7/2012 | Foo et al. |
| 2012/0254987 A1 | 10/2012 | Ge |
| 2013/0308506 A1 | 11/2013 | Kim |
| 2014/0211973 A1 | 7/2014 | Wang et al. |
| 2015/0172831 A1 | 6/2015 | Dittberner |
| 2015/0199977 A1 | 7/2015 | Ungstrump et al. |
| 2015/0222999 A1 | 8/2015 | Rasmussen et al. |
| 2015/0237450 A1 | 8/2015 | Schmidt |
| 2015/0270288 A1 | 9/2015 | Zamazaki et al. |
| 2015/0281863 A1 | 10/2015 | Westergaard et al. |
| 2015/0351143 A1 | 12/2015 | Seymour et al. |
| 2016/0150330 A1 | 5/2016 | Niederberger |
| 2016/0174001 A1 | 6/2016 | Ungstrup et al. |
| 2016/0212552 A1 | 7/2016 | Schneider et al. |
| 2017/0180886 A1 | 6/2017 | Van Der Loo |
| 2020/0098475 A1 | 3/2020 | Westermann et al. |

FOREIGN PATENT DOCUMENTS

| | | |
|---|---|---|
| EP | 1 843 634 A2 | 10/2007 |
| EP | 2 070 385 A2 | 6/2009 |
| EP | 2 227 041 A1 | 9/2010 |
| EP | 2 760 225 A1 | 7/2014 |
| EP | 2 799 985 A2 | 11/2014 |
| JP | 2001-142766 A | 5/2001 |
| JP | 2014-204145 A | 10/2014 |
| WO | 2007/020299 A2 | 2/2007 |
| WO | 2007/144435 A2 | 12/2007 |
| WO | 2011/128462 A2 | 10/2011 |
| WO | 2011128462 A2 | 10/2011 |
| WO | 2013/117214 A1 | 8/2013 |
| WO | 2014/094859 A1 | 6/2014 |
| WO | 2014/094866 A1 | 6/2014 |

OTHER PUBLICATIONS

Communication dated May 22, 2018 from the Japanese Patent Office in counterpart Application No. 2017-523439.
International Search Report for PCT/EP2014/075111 dated Sep. 21, 2015 [PCT/ISA/210].

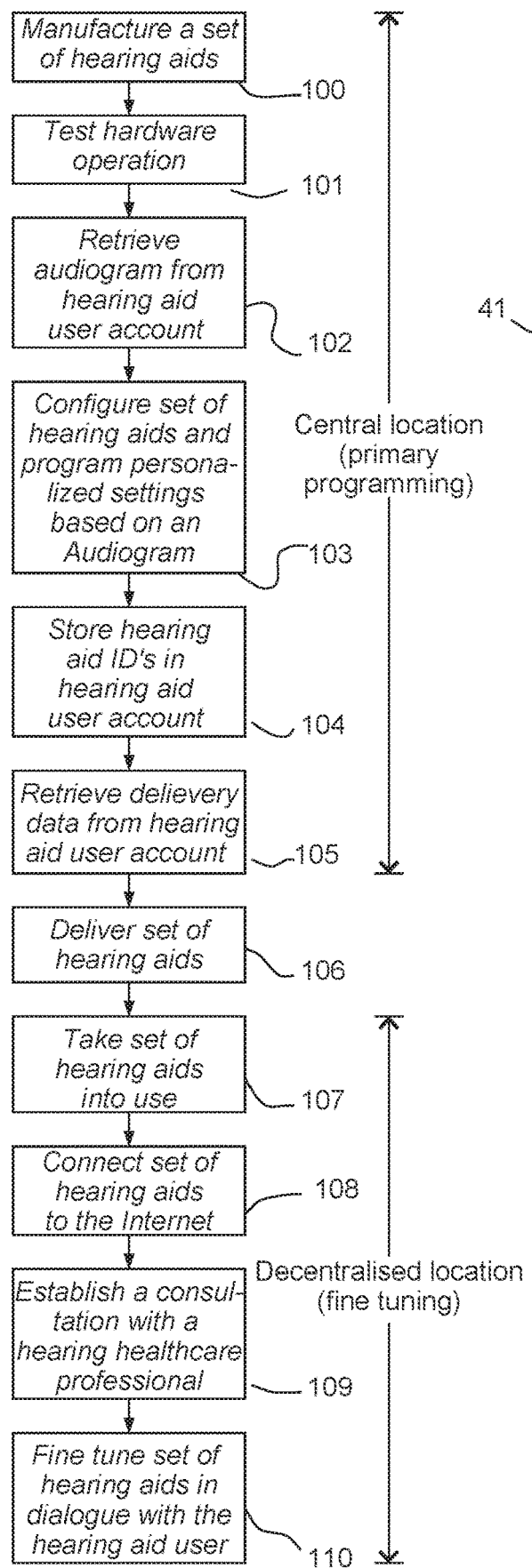
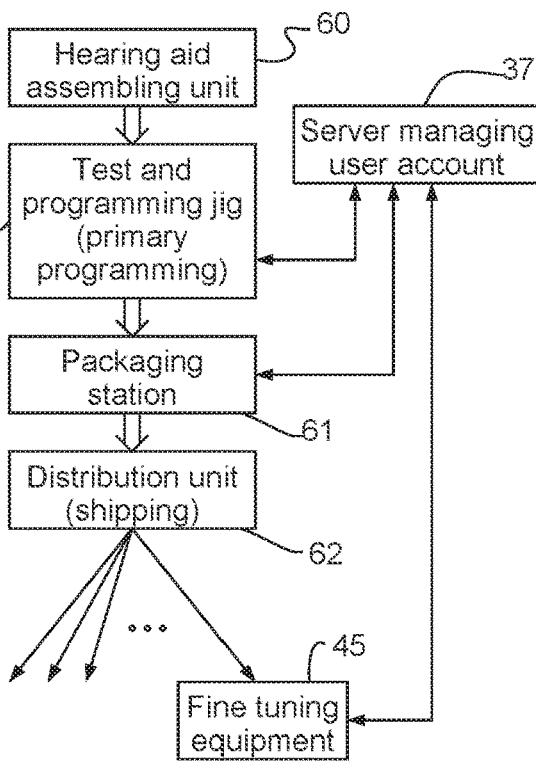
Fig. 4
Fig. 5

SYSTEM AND METHOD FOR PERSONALIZING A HEARING AID

CROSS REFERENCE TO RELATED APPLICATIONS

This application a Continuation Application of U.S. application Ser. No. 15/752,479, filed Feb. 13, 2018, which is a National Stage of International Application No. PCT/EP2015/068762 filed Aug. 14, 2015, the entirety of the disclosures of which are incorporated herein by reference.

BACKGROUND OF THE INVENTION

The present invention relates to hearing aids. The invention, more particularly, relates to a method for personalizing a hearing aid. The invention also relates to a system for personalizing a hearing aid.

When fitting a hearing aid, the initial fitting appointment is rarely sufficient, and multiple follow-up visits are often necessary. Most audiologists provide an up-to-date audiogram at the time of purchase.

Recently, hearing aids with wireless connectivity based on an open telecom protocol have reached the market. Binaural hearing aids based on proprietary communication protocols have been on the market for a decade. The Bluetooth connectivity is the most recent innovation in wireless interfacing for hearing instruments to audio sources such as TV streamers or mobile phones. Basically the fitting requires setting of a set of parameters. Hearing aids are quite small, and computer-wise most hearing aid have difficulties in handling major batches of software received in data packets as the hearing aids are missing a working memory of sufficient size. The preferred open telecom protocol has data packet size far too limited to handle the entire set of parameters to set in a few data packets.

SUMMARY OF THE INVENTION

The purpose of the invention is to provide a method of personalizing a set of hearing aids without requiring multiple follow-up visits at the audiologists.

This purpose is according to the invention achieved by a method of personalizing at least one hearing aid for a hearing aid user. The method comprises manufacturing at least one hearing aid at a manufacturing facility, receiving an audiogram from a server for the hearing aid user, programming the at least one hearing aid in a programming station of the manufacturing facility by means of the audiogram, whereby the at least one hearing aid becomes personalized for the hearing aid user, packaging, in packaging station of the manufacturing facility, the at least one hearing aid for distribution, and delivering the at least one personalized hearing aid to the hearing aid user.

Advantageously a consultation between the hearing aid user and a hearing healthcare professional having equipment for fine tuning the hearing aid may hereafter be set up. The fine tuning equipment is connected to the at least one personalized hearing aid, and the fine tuning of the at least one personalized hearing aid is carried out in dialogue between the hearing healthcare professional and the hearing aid user. Hereby the primary programming of the hearing aid may take place in the factory environment—preferably when the hearing aid is placed in a jig for testing. The jig for testing the hearing aid then preferably includes the programming station. The programming may then in one embodiment be carried out by means of a reliable wired programming connection. Hereafter, the hearing aids only need fine tuning.

The fine tuning takes place in dialogue between a hearing healthcare professional and the hearing aid user. Often the hearing healthcare professional presents the user for one or more sound environments, and based upon the feedback from the hearing aid user, the hearing healthcare professional corrects a limited number of parameters in the overall parameter set for personalizing the hearing aid. Bluetooth Low Energy will become the de facto standard for the connectivity between hearing aid and connected devices like smartphones, PC's, tablets, televisions etc. Bluetooth Low Energy with an appropriate audio codec will become the standard for audio streaming to hearing aids. The challenge for a hearing aid is that the hearing aid lacks computing resources, so the hearing aid is not able to receive and temporarily store data for subsequently overwriting a current setting. The challenge of Bluetooth Low Energy is that data is sent as packets, the data packets having a payload between 2 to 39 bytes. By providing the programming as a step programming according to the invention, the fine tuning may be carried out by adjusting individual parameter which may take place by sending data in a single data packet and write data in the appropriate memory location. Several parameters may be adjusted by repeating the step of transmitting and writing for several successive data packets.

According to a second aspect of the invention there is provided a hearing aid delivering system for personalizing one or more hearing aids. The hearing aid delivering system includes at a server managing user accounts for a plurality of hearing aid users, said user accounts including an audiogram for a hearing aid user, and a programming station adapted to receive said one or more hearing aids and programming instructions from said server for pre-programming said one or more hearing aids by means of the audiogram, whereby said one or more hearing aids become personalized for alleviating the hearing loss of the hearing aid user.

Preferably the hearing aid delivering system includes programming equipment for, during fine tuning in consultation between the hearing aid user and a hearing healthcare professional, to be connected to the hearing aid, whereby the hearing healthcare professional connects his fine tuning equipment to the at least one personalized hearing aid, and carries out the fine tuning of the at least one personalized hearing aid in dialogue with the hearing aid user.

According to a third aspect of the invention there is provided an hearing aid personalization system for personalizing at least one hearing aid for a hearing aid user, wherein the hearing aid personalization system is present in a manufacturing facility and receives said at least one hearing aid. The hearing aid personalization system comprises a server managing accounts including personal information and audiograms for a plurality of hearing aid users a programming station for programming the at least one hearing aid by means of a audiogram received from the server, whereby the at least one hearing aid becomes personalized for the hearing aid user, a packaging station for packaging the at least one hearing aid, and a distribution unit for delivering the at least one hearing aid to the hearing aid user based on personal information received from the server.

According to a fourth aspect of the invention there is provided an Internet enabled personal communication device for use in hearing aid delivering system according to the second aspect of the invention. The Internet enabled personal communication device comprises a wireless transceiver for establishing a short range wireless connection to the at least one hearing aid, and a processor for executing fitting software program allowing a hearing healthcare professional to fine tune the at least one personalized hearing aid in dialogue with the hearing aid user, wherein said processor is adapted to retrieve data relating to the pre-programming of the at least one hearing aid from a remote server via the internet.

According to a fifth aspect of the invention there is provided a computer-readable storage medium having computer-executable instructions, which, when executed in an Internet enabled personal communication device, are adapted for providing a user-interface for a hearing healthcare professional for fine tuning the at least one personalized hearing aid in dialogue with the hearing aid user, and retrieving data relating to the pre-programming of the at least one hearing aid from the remote server via the internet and presenting the data in the user interface.

According to a sixth aspect of the invention there is provided a computer-readable storage medium having computer-executable instructions, which, when executed in an Internet enabled personal communication device acting as a gateway between at least one hearing aid and a remote server accessible over the Internet, are adapted to providing a real-time direct, encrypted communication channel between an end-user client defined by the computer-executable instructions and the at least one personalized hearing aid, said communication channel allowing a hearing healthcare professional to fine tune the at least one personalized hearing aid in dialogue with the hearing aid user.

BRIEF DESCRIPTION OF THE DRAWINGS

The invention will be described in further detail with reference to preferred aspects and the accompanying drawing, in which:

FIG. 4 illustrates a flow chart for programming a set of hearing aids according to one embodiment of the invention;

FIG. 5 illustrates the handling flow according to one embodiment of the invention;

DETAILED DESCRIPTION

Figure 1:
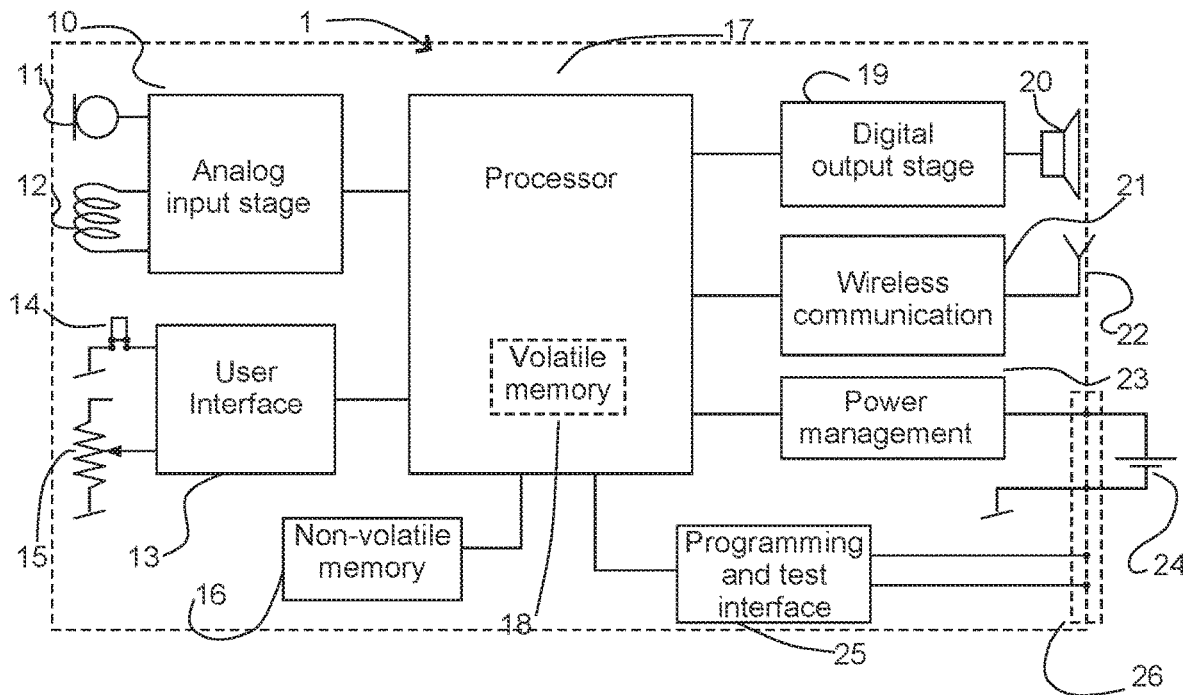
FIG. 1 illustrates schematically a hearing aid according to an embodiment of the invention.

Reference is made to FIG. 1, which schematically illustrates a hearing aid 1 manufactured and personalized for a hearing aid user according to a first embodiment of the invention.

On the input side, the hearing aid 1 comprises an analog input stage 10 receiving input from one or more acoustical-electrical input transducer 11 for picking up the acoustic sound and a telecoil 12. The analog input stage 10 pre-amplifies and converts the analog audio signals from the input transducer 11 and the telecoil 12 into digital signals, and the analog input stage 10 feeds the digital signals to a processor 17.

The hearing aid 1 includes a standard hearing aid battery 24 and a power management unit 23 ensuring that the various components are powered by predetermined stable voltages regardless of the momentary voltage value defined by the discharging curve of the battery 24.

A wireless communication unit 21 includes an antenna 22 for communication with other devices via a short range communication link. Such a short range communication link may be provided by Bluetooth™ Low Energy which is a wireless technology standard for exchanging data over short distances (typically less than 10 m), operating in the same spectrum range (2402-2480 MHz) as Classic Bluetooth technology. However other standards—like WLAN or proprietary standards—may be applicable if a wide availability and low power consumption is present. A Bluetooth Core System consists of an RF transceiver, baseband (after down conversion), and protocol stack (SW embedded in a dedicated Bluetooth™ Integrated Circuit. The system offers services that enable the connection of devices and the exchange of a variety of classes of data between these devices.

The wireless communication unit 21 has a digital interface towards the processor 17, and delivers digital signals to the processor 17 based upon the radio signal received by the antenna 22, and these digital signals includes an indication of the type of data and the actual payload. The payload may be control signals controlling the operation of the hearing aid, audio data representing audio streamed to the hearing from a remote device like a smartphone paired with hearing aid, a smart television or another device having audio streaming capabilities matching the wireless communication interface of the hearing aid 1. The payload may also be audio signals or control signals from a similar hearing aid 1 in a pair of binaural hearing aids.

The processor 17 is a digital signal processor adapted for amplifying and conditioning of the audio signal intended to become presented for the hearing aid user. The amplification and conditioning is carried out according to a predetermined setting in order to alleviate a hearing loss by amplifying sound at frequencies in those parts of the audible frequency range where the user suffers a hearing deficit.

According to one embodiment of the invention, the processor 17 includes an inherent volatile memory 18 requiring power to maintain the stored information. The content of the volatile memory 18 is erased every time the hearing aid is switched off. The processor 17 further includes a non-volatile memory 16 which retains stored information even when not powered. The predetermined setting in order to alleviate a hearing loss is stored in the non-volatile memory 16, while control settings input by the user in order to adjust the volume, select an acoustical program or activate audio input source are stored in the volatile memory 18. The non-volatile memory 16 contains default settings to be read into the volatile memory 18 when powering on the hearing aid. Examples of non-volatile memories are flash memory, EPROM or EEPROM memory used for firmware such as boot programs. Examples of volatile memory are various types of RAM.

The hearing aid 1 has a user interface unit 13 including a push button 14—e.g. for toggling between the hearing aid programs—and a potentiometer 15 for volume control. The user interface unit 13 transfers the input to the processor 17 storing the user input in the non-volatile memory 18 for controlling the hearing aid.

The processor 17 outputs according to one embodiment of the invention a digital a digital signal fed to a digital output stage 19 including a Delta-Sigma-converter providing an electrical output signal formed as a one-bit digital data stream fed directly to an output transducer 20, i.e. the output converter drives the transducer 20 directly as a class D amplifier.

Hearing aid programming includes two different aspects—acoustic programming refers to setting parameters (e.g. gain and frequency response) affecting the sound output to the user, which carries risk of potentially damaging the residual hearing by making wrong settings; and operational programming refers to settings which do not affect the sound significantly, such as volume control and selection of environmental programs. The programming steps according to the invention refer to acoustic programming.

The battery 24 is in normal operation used for powering on the hearing aid 1, and in the illustrated embodiment, the battery 24 is preferably one of a plurality of standardized hearing aid battery types which are uniquely identified via a color code and a size number—including yellow/size 10, brown/size 312, orange/size 13, and blue/size 675. When the battery 24 is removed and the battery door (not-shown) is opened, one can access the interior of the battery compartment. Hereby a test and programming connector interface 26 become available for programming and testing the hearing aid 1 prior to leaving the manufacturing facility. Hereby it is possible to place the hearing aid 1 in a test and programming jig 41 (FIG. 2) having a plug to be received in the empty battery compartment. The plug has a plurality of test and programming connector parts interoperating with the test and programming connector interface 26 inside the empty battery compartment. The plug will power on the hearing aid by applying a stable battery voltage to a battery connector pin and ground via a ground pin. Two further connector pins are indicated—one serial signal input and one serial signal output. The test and programming connector interface 26 may however include additional connector pins, e. g. if parallel signal input/output is applied.

The test and programming connector interface 26 is used to run some test routines of the hearing aid 1 prior to the shipping from the manufacturing facility. Hereby, it becomes possible to verify that the hearing aid 1 operates within the specifications when leaving the manufacturing line. According to one embodiment, the test and programming connector interface 26 is used for programming a pair of hearing aids 1 according to a prescription developed to reach a setting where the pair of hearing aids 1 will alleviate a hearing loss of a specific user by amplifying sound at frequencies in those parts of the audible frequency range where the specific user suffers a hearing deficit.

This programming is based upon an audiogram made available for the manufacturing facility. Hereby the hearing aids 1 become personalized prior to leaving the manufacturing facility; and the programming at the manufacturing facility becomes a first fitting step which takes place in a factory environment based on uploading of the audiogram of the and user. This is beneficial as the first fitting step takes place as part of a manufacturing facility environment where technicians in the manufacturing facility are expert in manipulating the hearing aids, and the test and programming jig 41 is dedicated for this sole purpose. The number of items passing through the test and programming jig 41 is higher compared to normal fitting at a local (decentralized) fitter or audiologist, and as a consequence the test and programming jig 41 can be optimized with regard to programming speed, but also with regard to security as a part of the programming may include a software controlled configuration of the hearing aid—defining features like number of processing bands for the processor 17, transposing or compressing audio input bands into lower bands where the hearing aid user actually does have some residual ability to hear, or other user specific programmable features. This affects the selling point of the hearing aids 1, and this may therefore be subject to organized fraud. By doing the essential part of the programming internally in manufacturing facility environment, the number of test and programming jigs 41 is reduced significantly, and the management of programming software becomes safer. By having the first fitting step to take place in the manufacturing facility environment, the need for having a common programming interface serving all manufacturing brands will be eliminated.

Figure 2:
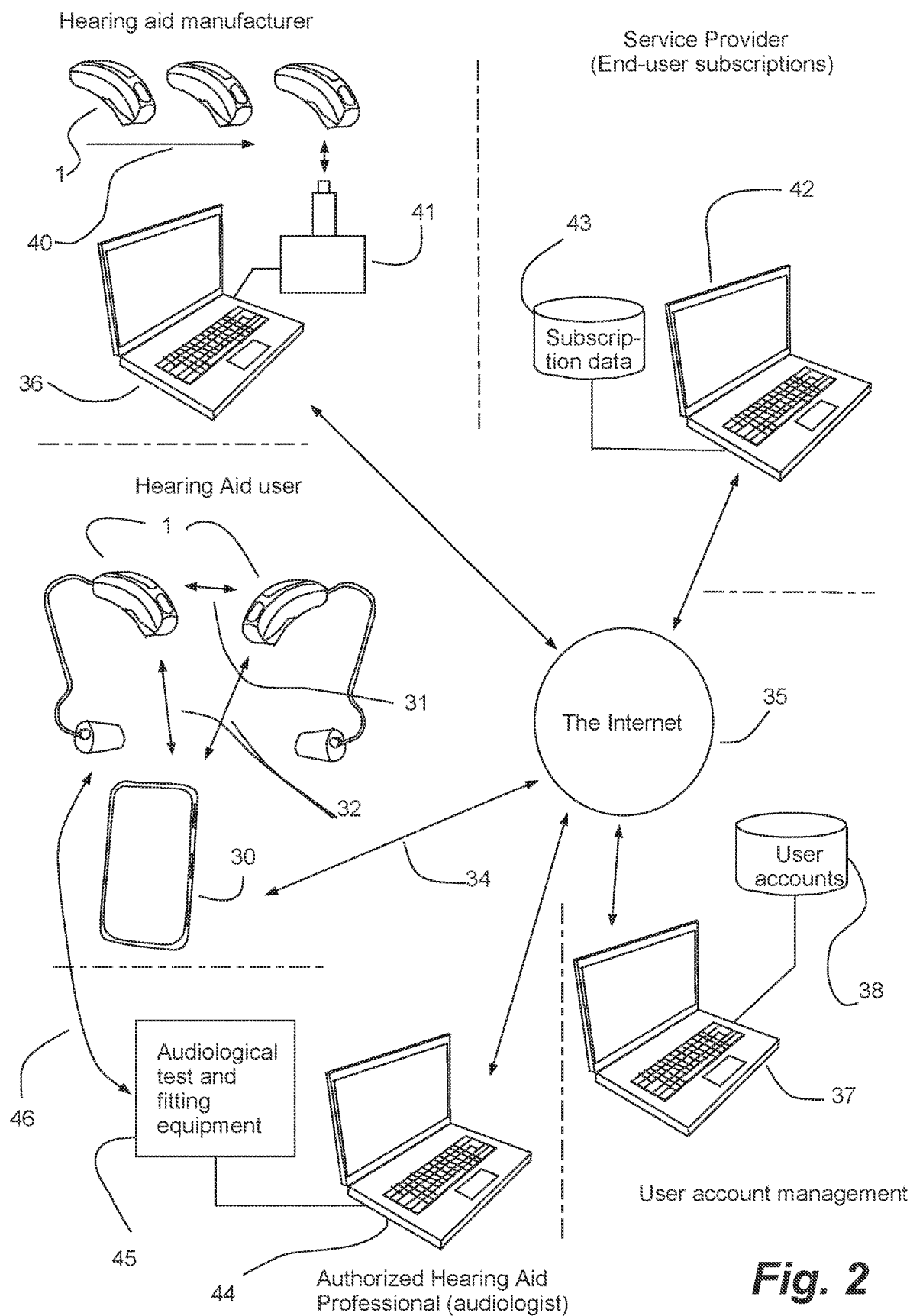
FIG. 2 illustrates schematically the interaction of the hearing aids during the programming according to an embodiment of the invention.

FIG. 2 shows a set of hearing aids 1 having an inter-ear communication channel 31, preferably based on a proprietary communication protocol or the Bluetooth™ Low Energy protocol, which is preferred for the communication between the set of hearing aids 1 and a personal communication device 30—here shown as a smartphone. By using a proprietary communication protocol for the inter-ear communication channel 31, it is possible to optimize the inter-ear communication channel 31 with regard to power consumption, while by using the Bluetooth™ Low Energy protocol for the inter-ear communication channel 31, it is possible to reduce the number of radios required in the hearing aid. The set of hearing aids 1 is illustrated as Behind-The-Ear hearing aids having customized ear plugs. However the invention is applicable for any type of hearing aids, assistive hearing devices or assistive hearing systems being able to communicate with an external device via the wireless connection 32.

The personal communication device 30 according to the invention is Internet enabled, which means that the personal communication device 30 may access the Internet 35 via a connection 34. The connection 34 is preferably a wireless Internet connection, (e.g. wireless local area network (WLAN) based on IEEE 802.30 standards) or a cellular data connection (e.g. WCDMA or LTE). Advantageously, the personal communication device 30 has the ability to download and launch application software from a remote server on the Internet, e. g. an app store. Furthermore, the personal communication device 30 will be able to access via the Internet 35 a master server 37 having user data storage 38 for maintaining and storing a plurality of hearing aid user accounts.

The term "app" is short for "application software" which is a set of one or more programs designed to carry out operations for a specific application. Application software cannot run on itself but is dependent on system software to execute.

The hearing aid user may from the personal communication device 30 or from a computer 36 via an appropriate Internet connection access the master server 37 for inspecting or editing his own user account. Accessing user data stored on the master server 37 requires that the hearing aid user has the required access rights.

The hearing aid manufacturing company has according to one embodiment a manufacturing facility having a computer 36 controlling at least a part of the manufacturing process, and this computer 36 is connected to the test and programming jig 41. The hearing aids 1 are transported on a conveyor 40 and transferred automatically or manually to the test and programming jig 41 for testing and programming. The computer 36 accesses the master server 37 via an appropriate Internet connection for retrieving orders from customers, and sets the setting of the hearing aid 1 by programming. When tested and programmed, the personalized hearing aids 1 are shipped to the designation indicated in the user account, and the manufacturing company updates the user account stored in the user data storage 38.

Entities distributing the hearing aids from the manufacturing companies to the hearing impaired customer may, as assisting service providers dealing with e.g. end-user subscriptions from a service provider server 42 via an appropriate Internet connection, access the master server 37 having user data storage 38 for maintaining and storing hearing aid user accounts—or at least relevant parts of the hearing aid user accounts. The service provider server 42 is connected to a data storage 43 containing subscription data for a plurality of hearing impaired customers being customers at the entity. The entity may be a specialty store, a factory owned store, a supermarket, an Internet shop, a membership warehouse club, a discount store or the like. Accessing user data stored on the master server 37 requires that the entity representative has proper/appropriate access rights.

Finally, authorized hearing healthcare professional or audiologists may from a computer 44 via an appropriate Internet connection access the master server 37 having user data storage 38 for maintaining and storing hearing aid user accounts. Accessing user data stored on the master server 37 requires that the authorized hearing healthcare professional has the appropriate access rights. The authorized hearing aid professionals have audiological test and fitting equipment 45 for measuring and estimating the hearing loss of the customer, and subsequently fitting a set of hearing aids 1 compensating for the unique hearing loss of the customer. According to one embodiment of the invention, an authorized hearing healthcare professional creates an audiogram based on his audiological tests and uploads the audiogram to the user account maintained by the master server 37, from where it is retrieved by the manufacturer for personalizing the requested set of hearing aids 1.

As the essential step in fitting process has been taken at the manufacturing facilities, only the fine tuning—if required—is left and this may take place as an interactive and iterative process. Therefore the audiological test and fitting equipment 45 is adapted for wireless communication directly with hearing aids 1 via a data link 46. The data link 46 may be provided by means of a proprietary communication protocol used for the inter-ear communication channel 31, or by means of the Bluetooth™ standard, e.g. according to Bluetooth™ Low Energy protocol, which is preferred for the communication between two hearing aids 1 and the personal communication device 30.

Figure 3:
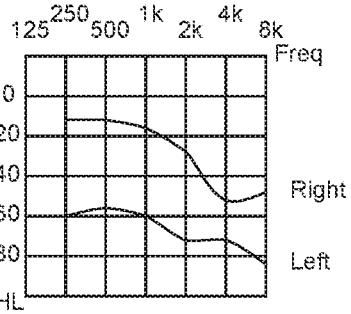
FIG. 3 illustrates an example of a schematic representation of a user account according to one embodiment of the invention.

According to one embodiment illustrated with reference to FIG. 3, the user account created and maintained in the server 37 by the user and hearing professionals permitted by the user contains a data set 50. The data set 50 includes a personal information data field 51, which typically is the first data field filled out by the user when creating an account. The personal information includes name, address and additional contact data like phone number and e-mail address. A delivery address data field 52 defines the delivery address for hardware to be delivered to the hearing aid user. This hardware may include hearing aids returned from service, replacement hearing aids, batteries, wax guards, hearing aid drying boxes and other items ordered from the service provider or the manufacturer. The delivery address is specified by the owner of the account and may be identical to the home address identified in the personal information data field 51, may identify a preferred pick up place (e.g. a medical house) or may identify a preferred pick up place in case the account is linked to a membership in a warehouse club.

In a social security data field 53, the user may enter his birthday information and social security number, which may be used by the social authorities in cases these are committed to pay a part of the sales prize or subscription fees.

In an accounting data field 54, the manufacturer, the service provider, and the authorized hearing aid professional may enter respective service agreements and the user may enter billing details, such as that an invoice is preferred or that an amount to be drawn from a specified credit card is preferred. The service agreements may refer to a specified fitting session, a hearing test, purchase of a specified set of hearing aids, subscription to a specified set of hearing aids, upgrade of an existing set of hearing aids, batteries, or replacement parts. The user has the right to approve the service agreements and enter billing details, while the service providers may enter service agreement details as price and conditions supported by one or more documents and use entered billing details for their own accounting. The accounting data field 54 will only contain one service agreement, and if several service agreements are initiated, supplementing accounting data fields 54 will be created. Only parties to a service agreement do have Data Retrieval Rights to these data fields 54.

The data set 50 includes a dedicated Hearing Loss Characterization data field 55 containing data representing the hearing loss of the user account owner.

In one embodiment, an authorized hearing healthcare professional or audiologist tests the hearing of the user account owner. The audiologist obtains the results in an audiogram measured by an audiometer. The audiometer is test equipment used for evaluating hearing loss of a patient. Audiometers are standard equipment employed at ear-nose-throat clinics and in audiology centers. An audiometer usually includes a hardware unit connected to a pair of headphones, a test user interface operated by the patient, and a control user interface operated by the hearing healthcare professional or the audiologist. The control user interface may be a standard Personal Computer, a tablet PC, or a similar computing device. The audiogram is a graph showing the hearing loss measured in decibels for standardized frequencies in Hertz. The threshold of hearing is plotted relative to a standardized curve (0 dB) that represents "normal" hearing, in dB (HL). The audiologist may store the audiogram in the dedicated Hearing Loss Characterization data field 55.

In a second embodiment, the audiologist tests the hearing of the user account owner. The audiologist utilises in-situ audiometry, which takes into account the individual characteristics of the ear canal and the hearing aid—giving a more precise basis for a successful fitting. By means of in-situ audiometry the user's hearing threshold is measured in a plurality of basic frequency bands and represented in an audiogram with in-situ measurements such as so-called Sensogram™ (trademark of the applicant). The main advantage of using the Sensogram™ is that it renders the first fitting of the hearing aid closer to the target, which means that less fine tuning is needed. The audiologist may store the Sensogram™ in the dedicated Hearing Loss Characterization data field 55.

In a third embodiment, the hearing of the user account owner is tested by means of a private computer. As older adults become more information technology-savvy, there has been developed quick online hearing screening tests to support the early detection and treatment of hearing loss. The online hearing screening shall assess the hearing threshold of the user without relying upon the user to calibrate the volume. This purpose is fulfilled by an adaptive logatome hearing screening method determining the presence of hearing loss by measuring the Speech Reception Threshold (SRT) of the user in fluctuating noise. A logatome stimulus is presented (audio/speech) at various levels (adaptively) along with a fluctuating speech noise presented at a constant level, and the test person has to identify the played stimuli among a plurality of related logatomes presented graphically on a display. The Speech Reception Threshold in fluctuating noise increases significantly for those with hearing loss, this information is compared against established norms to yield a screening test result. The test shows sufficiently good result for use as input for estimating an audiogram for the tested hearing account owner. The user downloads the hearing test from the service provider server 42, and the estimated audiogram for the tested hearing account owner is automatically entered into the Hearing Loss Characterization data field 55 in the user account in the master server 37.

In a fourth embodiment, the hearing of the user account owner is tested by means of a private computer. A hearing loss might be inherited from parents or acquired from illness, ototoxic (ear-damaging) drugs, exposure to loud noise, tumors, head injury, or the aging process. However mild and moderate hearing loss may be estimated by means of a simple questionnaire, as it has been recently understood that certain factors affect the hearing loss. These factors includes age, sex (men's hearing degrades faster than women's), birth weight (low birth weight causes faster degrading of hearing), and noise exposure (soldiers, hunters, musicians and people working in noisy environments do have a faster degrading of hearing). Other factors degrading the hearing includes smoking, exposure to radiation therapy and chemotherapy, extensive use of pain relievers and certain antibiotics, and diseases like diabetes and sleep apnea. The answers to a simple questionnaire show sufficiently good result for use as input for estimating an audiogram for the tested hearing account owner. The user downloads the questionnaire from the service provider server 42, and the estimated audiogram for the tested hearing account owner is automatically entered into the Hearing Loss Characterization data field 55 in the user account in the master server 37.

According to the invention at least one hearing aid 1 becomes personalized for a hearing aid user in two steps. The first step takes place at a centralized location—e.g. in a test and programming station 41 as a part of the manufacturing facility, or in a programming station 41 at the distribution center. The test and programming station 41 is optimized with regard to labor efficiency. The test and programming station 41 receives an audiogram from the server 37 for the specific hearing aid users and receives hearing aids from the manufacturing line 40. The test and programming station 41 programs hereafter the hearing aid by means of the audiogram, whereby the at least one hearing aid becomes personalized for the hearing aid user. Once a hearing aid 1 has been approved in the testing process and programmed based upon the audiogram in the dedicated Hearing Loss Characterization data field 55 of a user account, the test and programming station 41 enters the product ID data read from the memory of the hearing aid 1 into a dedicated hearing aid ID data field 57 of the user account in the master server 37. The product ID data may include hearing aid model, serial number, software and firmware version, and identify special hardware if required. The test and programming station 41 also enters the settings for alleviating the hearing loss calculated based on the audiogram into a hearing compensation profile data field 56. Afterwards, an authorized hearing aid professional will for his clients have Data Update Rights to the Hearing Loss Characterization data field 55 and the hearing compensation profile data field 56.

As a part of the programming the test and programming station 41 will retrieve the delivery address from the delivery address data field 52, and print a label based on the delivery address, and the least one personalized hearing aid 1 can be delivered to the address specified by the hearing aid user.

For each user account there is provided a data field 58 containing security elements including credentials for access to one or more data fields in the hearing aid user account and secure keys for establishing a secure connection between the master server 37 and the hearing aid 1.

The method of personalizing a hearing aid 1 according to the invention may be regarded as a fitting process where the primary programming takes place prior to the hearing aid leaves the factory or as a hearing aid on demand service. In some cases the personalized hearing aid 1 needs fine tuning, and this fine tuning then takes place in a consultation with a hearing healthcare professional.

The method will now be described with reference to FIGS. 4 and 5. In step 100, a hearing aid 1 is manufactured in a hearing aid assembling unit 60 in a per se known manner, and in step 101 the manufactured hearing aid 1 is placed in the test and programming jig 41, where the performance of the manufactured hearing aid 1 is tested. In step 102, the computer 36 retrieves the audiogram from the user account in the master server 37, and in step 103, the set of hearing aids 1 is configured and personalized settings are programmed based on the audiogram. In step 104, the computer 36 retrieves the hearing aid ID from the hearing aid 1 and stores the Hearing aid ID in the user account in the master server 37. In step 105, the computer 36 retrieves the delivery address from the user account in the master server 37, and adds this information to the programmed set of hearing aids 1 forwarded to a packaging station 61 for packaging and labelling. From a distribution unit 62 the hearing aids are shipped to the customer, and the delivering takes place in step 106. The primary programming or personalization takes place at a central location—preferably at the manufacturing facilities—in steps 100-105. The primary programming is in one embodiment based upon a wired connection between the hearing aid 1 and the test and programming computer 36, however in some circumstances a wireless connection may be applicable.

In step 107, the hearing aid user receives his set of hearing aids 1—either at home or at the audiologist, and he brings the hearing aids 1 into use by inserting batteries and placing the hearing aids 1 in his ears. In step 108, the user pairs his new hearing aids 1 with his personal communication device 30. The benefit of using Bluetooth™ Low Energy is that many different personal communication devices 30 like smartphones, hearing aid streamers, tablet PC's and laptops already support the standard, whereby the hearing aid 1 by pairing with one of these personal communication devices 30 can use the personal communication device 30 as a gateway to the Internet 35.

When the set of hearing aids 1 has been connected to the Internet, the user may start using the hearing aids 1 as the hearing aids 1 have already been personalized based on the users audiogram. If a need for correction occurs, the user may request a consultation a hearing healthcare professional having equipment 45 for fine tuning the hearing aids 1 is established in step 109. The hearing healthcare professional connects his fine tuning equipment 45 to the hearing aids 1 and fine tuning the hearing aids 1 in dialogue with the hearing aid user in step 110. The fine tunes programming takes place at a location remotely (decentralized) from manufacturing facilities—preferably at the hearing care professional or at home of the hearing aid user—in steps 109-110. As it will appear from the description below, the steps of fine tuning may employ an Internet based video chat, where the consultation between the hearing aid user and a hearing healthcare professional takes place over the Internet 35, while the actual fine tuning takes place by a programming channel set up by means of the master server 37 and uses the personal communication device 30 as a gateway to the hearing aids 1.

Figure 6:
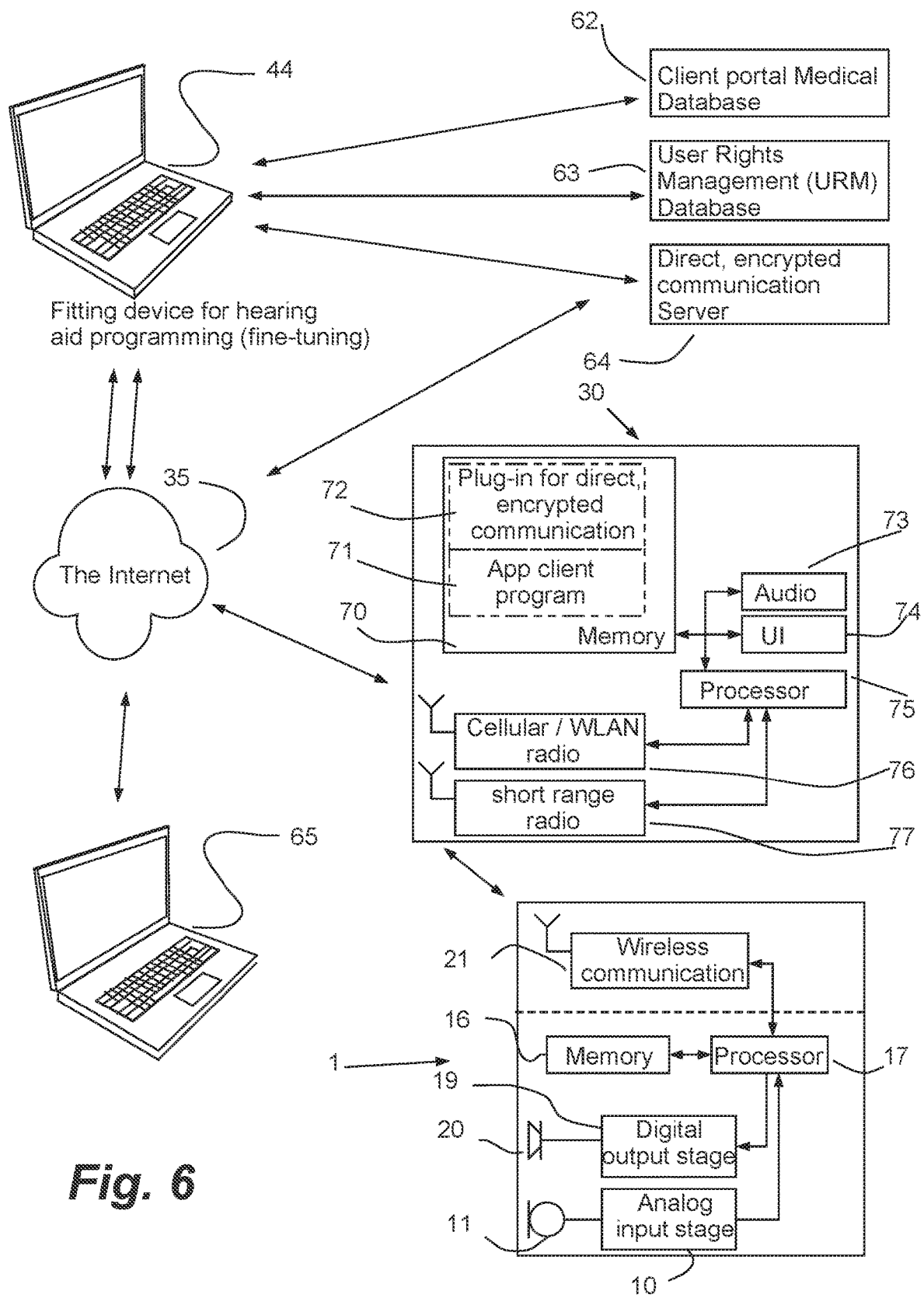
FIG. 6 illustrates schematically fine tuning programming of a hearing aid according to one embodiment of the invention.

A first embodiment for fine tuning the hearing aid 1 according to the invention is illustrated in FIG. 6. The hearing healthcare professional may be placed in a medical call center and he uses his computer 44 as equipment for fine tuning the hearing aids 1. When having a consultation with a hearing aid user, the hearing healthcare professional is able to access the user account in the master server 37—here named as a Client Portal Medical Database 62 by means of the computer 44. Hereby he will be able to inspect the stored audiogram, and inspect the current settings for alleviating the user's hearing loss. He will furthermore be able to retrieve the hearing aid ID from the dedicated hearing aid ID data field 57 and the necessary security elements from the security elements data field 58. The necessary security elements are here named as a User Rights Management (URM) Database 63 as these security elements defines what the hearing healthcare professional is permitted to do in relation to the reading and editing of the software setting of the hearing aid 1.

A server 64 provides real-time direct, encrypted communication between a remote session client running on the computer 44 and an app program 71 on the personal communication device 30. The platform for setting up the direct, encrypted communication includes a client plug-in to be integrated into the hearing aid programming client from which a hearing healthcare professional would like to establish a secure connection between a client communication devices (tablets, smartphones, computers) and resource limited devices (e.g. less than 1 kb RAM). The platform provides direct real-time connectivity with no firewall or dynamic IP issues. The platform for setting up the direct, encrypted communication furthermore includes a device plug-in for implementation in the resource limited device. Hereby each resource limited device is given a unique identity in a Domain Name System (DNS).

The remote session client on the computer 44 initiates a direct, encrypted connection to the hearing aid 1 via the personal communication device 30, and the communication server 64 mediates this direct connection. The unique identity in DNS of the hearing aid 1/personal communication device 30 is mapped to the IP address of the communication server 64, as the hearing aid 1/personal communication device 30 registers when online. The remote session client on the computer 44 is therefor able to look for available devices in this database, and therefore find the hearing aid 1/personal communication device 30 if online. Once the connection between the remote session client on the computer 44 and the hearing aid 1/personal communication device 30 has been established, the communication server 64 leaves the session. No data relating to a session are stored in the communication server 64.

The hearing aid programming client on the computer 44 may however also discover the device if located on the same LAN and communicate directly the hearing aid 1/personal communication device 30 without calling the communication server 64—which is useful for bootstrap scenarios or for offline sessions (direct Bluetooth Low Energy connection not involving the Internet). The hearing aid programming client contains the remote session client and uses this client for setting up the direct, encrypted connection to the hearing aid 1 via the personal communication device 30.

The hearing aid programming client may use the remote session client in different ways. The hearing aid programming client may be an HTML application that uses the remote session client to handle data in a JavaScript scripting language in a web application—in this scenario the remote session client is typically a web browser plugin or mobile app—preferably distributed from the communication server 64 to the hearing aid programming client and is denoted an HTML device driver bundle.

The customer's client application can also be a native (non-HTML) application, linked with a remote session client API library. The native hearing aid programming client application can use the same request/response mechanism to invoke the device as HTML applications do. Additionally, the native client can establish streaming data connections with the hearing aid 1/personal communication device 30—this is a popular way of adding seamless, secure remote access capabilities to legacy client and device applications.

For the hearing healthcare professional operating from a computer in e.g. a medical call center, the primary purpose for running the hearing aid programming client on the computer 44 is to be able to adjust the settings of a hearing aid 1. From the Client Portal Medical Database 62, the hearing healthcare professional is able to import the relevant data for the user and his hearing aids 1 into the client application. From the User Rights Management (URM) Database 63 the hearing healthcare professional is able to obtain the certificates require to perform the fine tuning of the hearing aid 1. By means of the IP address obtained from the communication server 64, the hearing aid programming client sets up a real-time direct, encrypted communication channel via the Internet 35, the personal communication device 30 and finally to the hearing aid 1. The hearing aid user may have a personal computer 65 next to him so he is able to see and have a conversation with the hearing healthcare professional via Skype® or another appropriate video chat platform.

The personal communication device 30 is associated with the hearing aid user, and it includes a cellular/WLAN radio 76 connecting the personal communication device 30 to the internet 35. A short range radio 77 connects the personal communication device 30 to the hearing aid 1 by means of the Bluetooth Low Energy protocol. Furthermore, the personal communication device 30 includes audio elements 73 (like a speaker and a microphone), UI elements 74 (like a touch screen or keys and a display), and a processor 75 controlling the operation of the personal communication device 30. The personal communication device 30 has memory 70 (e.g. EEPROM)—here containing a hearing aid specific app 71 and a plug-in for direct, encrypted communication 72 supporting programming of the hearing aid 1 from a remote computer 44. The hearing aid specific app 71 notifies the communication server 64 when the hearing aid 1 is available—either every time a Bluetooth connection is established or when the user actively confirms that a notification is needed.

By interviewing and providing sound examples for the user via the hearing aid, the hearing healthcare professional can make minor adjustment to the current settings and load these adjustments into the hearing aid1 via the secure communication channel set up. Bluetooth Low Energy protocol is specified in a way so a single data packet may contain between 2 to 39 bytes. An adjustment of the setting is preferably contained in one data packet.

Figure 7:
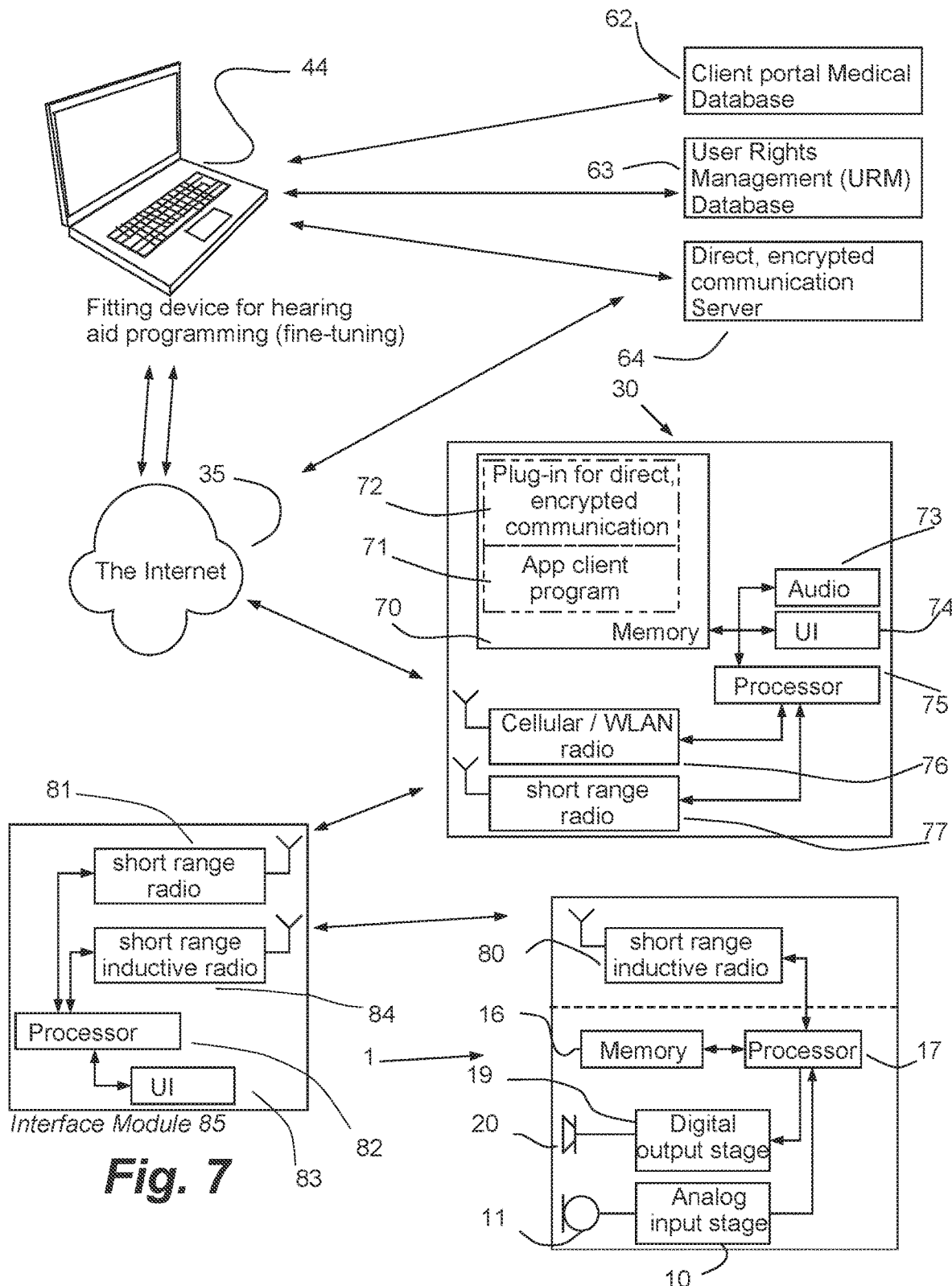
FIG. 7 illustrates schematically a fine tuning programming of a hearing aid according to another embodiment of the invention.

A second embodiment for fine tuning the hearing aid 1 according to the invention is illustrated in FIG. 7. This embodiment is similar to the embodiment shown in FIG. 6—apart from that the personal communication device 30 is connected to the hearing aid 1 via an Interface module 85. The interface module 85 has a first short range radio 81 communicating with the similar short range radio 77 in the personal communication device 30 using e.g. the Bluetooth Low Energy protocol. The interface module 85 has a second short range radio 82 communicating with the similar short range radio 80 in the hearing aid 1 using a power efficient proprietary protocol, which is preferred to be inductive. The interface module 85 has a UI element 83 for answering calls etc. and a processor 82 for translating data between the two wireless protocols. As the Interface module 85 is intended to be transparent between the personal communication device 30 and the hearing aid 1, the remote fine tuning will be similar to what is explained with reference to FIG. 6. However a parallel video call has been omitted in this embodiment.

Figure 8:
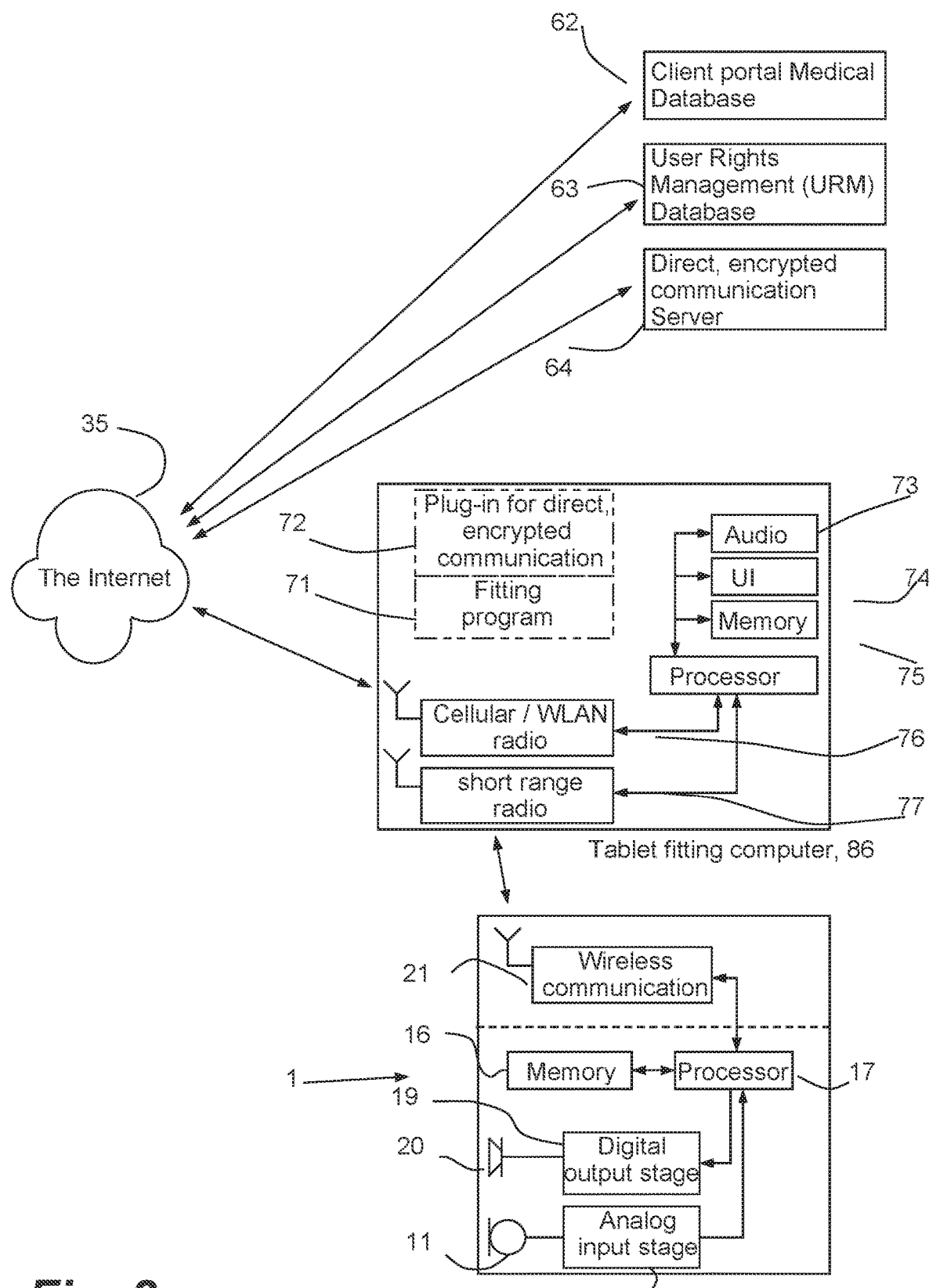
FIG. 8 illustrates schematically a fine tuning programming of a hearing aid according to a third embodiment of the invention.

A third embodiment for fine tuning the hearing aid 1 according to the invention is illustrated in FIG. 8. A table computer 86 is used in a face to face consultation between the hearing healthcare professional and the hearing aid user. The table computer 86 is paired with the hearing aid 1, and it has basically the same functionality as the personal communication device 30 in FIGS. 6 and 7. A direct Bluetooth Low Energy connection is set up between the table computer 86 and the hearing aid 1 (offline session) without having to call the communication server 64. In this scenario the fitting software for fine tuning the hearing aid 1 is running on the tablet computer instead of on the computer 44. However, the hearing healthcare professional is still able to import the relevant data for the user and his hearing aids 1 from the Client Portal Medical Database 62, into the client application now running on the tablet fitting computer 86, and to obtain the certificates require to perform the fine tuning of the hearing aid 1 from the User Rights Management (URM) Database 63.

As an alternative to the fine tuning process, the hearing aid 1 may include adaptive algorithms, so the hearing aid 1 in response to user input adapts the hearing aid setting (minor adjustment). This may be if the user corrects the volume shortly after entering a specific hearing aid program, like the music program. If the correction (e.g. 2 steps up in volume) is the same for a number of program shifts (e.g. 3), then the hearing aid 1 recognizes the correction to be a general correction requested by the user, and the specific program is adjusted accordingly (the volume of the music program is increased 2 steps) next time the specific program is entered. This may also be implemented audio environments and other specific listening situations.

Figure 9:
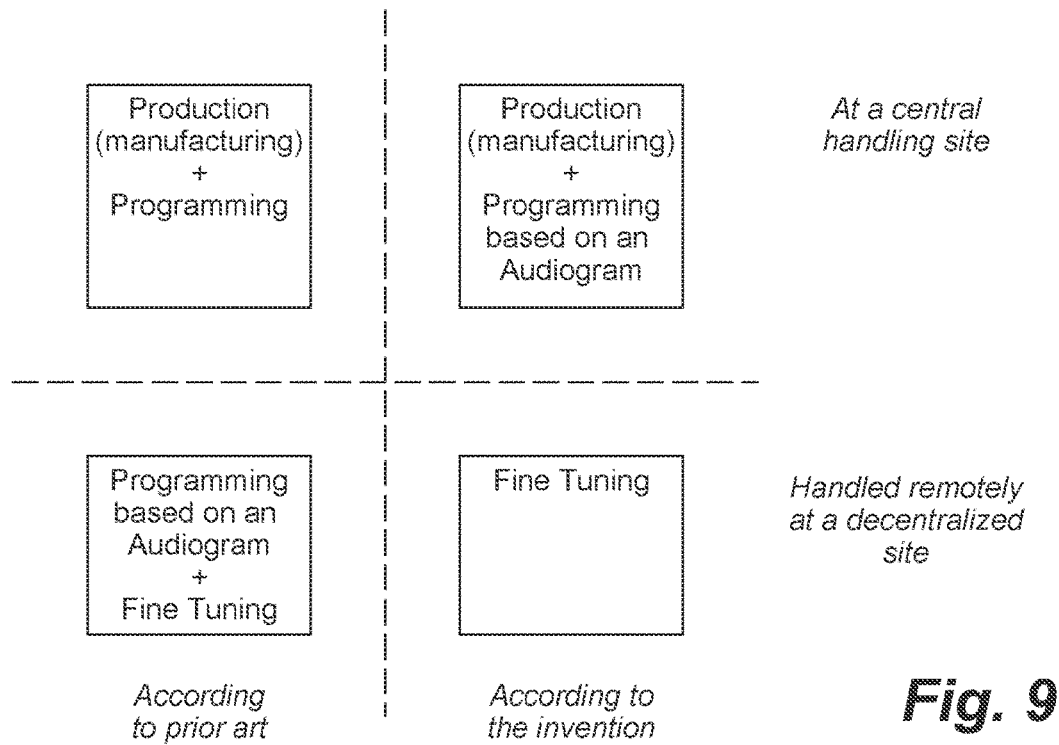
FIG. 9 compares the programming process according to one embodiment of the invention to a process according to the prior art.

FIG. 9 illustrates that the manufacturing and basic programming of a hearing aid traditionally has taken place centrally in the manufacturing facility, while the personalization of the hearing aid—including programming based on an audiogram and subsequent fine tuning has taken place at a distributed or remote site—typically by a hearing healthcare professional. The invention teaches how the audiogram of a hearing aid user may bring the personalization of the hearing aid—including programming based on an audiogram—to the central handling site where the programming may be performed more cost efficiently. The subsequent fine tuning—if needed—will now take place at a distributed or remote site—typically by a hearing healthcare professional. Hereby it becomes possible to employ new radio technology to fine tune a hearing aid having limited resources for handling software updates.

The invention claimed is:

1. A hearing aid personalization system for personalizing at least one hearing aid, comprising:
a server adapted for managing a database of user accounts for a plurality of hearing aid users, wherein the managing of a specific user account for a specific hearing aid user includes storing personal hearing loss information related to a hearing loss of the specific hearing aid user; and
a programming device configured to receive said personal hearing loss information from said server and to program said at least one hearing aid in accordance with said personal hearing loss information for alleviating a hearing loss for the specific hearing aid user, whereby the at least one hearing aid becomes personalized for the specific hearing aid user;
wherein said programming device is configured to program said at least one hearing aid prior to delivery of said at least one hearing aid to the specific hearing aid user.

2. The system according to claim 1, wherein said programming device is located at a facility of a hearing aid manufacturer.

3. The system according to claim 1, wherein said programming device is operated by a hearing aid manufacturer.

4. The system according to claim 1, wherein said personal hearing loss information comprises at least one of an audiogram for the specific hearing aid user or personal hearing aid settings determined in dependence on said audiogram and loadable into said hearing aid for alleviating said hearing loss.

5. The system according to claim 4, wherein the programming equipment is connectable to the at least one personalized hearing aid via a short range wireless connection for fine tuning the at least one personalized hearing aid in a face-to-face session.

6. The system according to claim 4, wherein said audiogram for each respective hearing aid user is derived at a location remote from said facility.

7. The system according to claim 1, wherein said system further includes a gateway at a location of said user for subsequently transferring personal hearing aid settings from said server to said hearing aid.

8. The system according to claim 1, wherein programming equipment for, during fine tuning in consultation between the hearing aid user and a hearing healthcare professional, can be connected to the hearing aid; whereby the hearing healthcare professional connects his fine tuning equipment to the at least one personalized hearing aid, and carries out the fine tuning of the at least one personalized hearing aid in dialogue with the hearing aid user.

9. The system according to claim 8, wherein an Internet enabled personal communication device and the at least one hearing aid are provided with respective transceivers for establishing a wireless connection, whereby the personal communication device becomes a gateway for the at least one hearing aid to the Internet; and wherein the programming device is an Internet enabled computer from which the hearing healthcare professional sets up the remote consultation with the hearing aid user and carries out the fine tuning of the at least one personalized hearing aid by using the personal communication device as a gateway.

10. A method of personalizing at least one hearing aid for a specific hearing aid user using the personalization system according to claim 1, said method comprising the steps of:
   managing said database of user accounts for said plurality of hearing aid users on said server;
   receiving at least a part of said hearing loss information for the specific hearing aid user from the specific user account for the specific hearing aid user for programming the at least one hearing aid for alleviating said hearing loss, whereby the at least one hearing aid becomes personalized for the specific hearing aid user; and
   delivering the personalized hearing aid to the specific hearing aid user.

11. The method according to claim 10, wherein said programming device is located at a facility of a manufacturer of said hearing aid.

12. The method according to claim 10, wherein said personal hearing loss information comprises at least one of an audiogram for the specific hearing aid user or personal hearing aid settings determined in dependence on said audiogram and loadable into said hearing aid for alleviating said hearing loss.

13. The method according to claim 10, comprising a further transferring step of transferring personal hearing aid settings from said server to said hearing aid over the Internet via a gateway.

14. The method according to claim 10, further comprising the steps of providing a consultation between the specific hearing aid user and a hearing healthcare professional having equipment for fine tuning the personalized hearing aid; connecting the fine tuning equipment to the personalized hearing aid; and fine tuning the personalized hearing aid in dialogue between the hearing healthcare professional and the specific hearing aid user.

15. The method according to claim 14, further comprising the steps of connecting the personalized hearing aid to the Internet; and said consultation between the specific hearing aid user and hearing healthcare professional is a remote consultation over the Internet; whereby the hearing healthcare professional carries out the fine tuning of the personalized hearing aid via the Internet.

16. The method according to claim 15, wherein the step of connecting the personalized hearing aid to the Internet includes connecting and pairing the personalized hearing aid with a personal communication device by using a short range wireless connection, whereby the personal communication device operates as a gateway to the Internet for the at least one personalized hearing aid.

17. The method according to claim 10, wherein the at least one hearing aid is programmed by configuring a signal processor of the hearing aid based on the personal hearing loss information for amplifying sound at frequencies in those parts of the audible frequency range where the user suffers a hearing deficit.

18. The method according to claim 17, wherein the programming of the at least one hearing aid includes applying a frequency transposition technique.

19. The method according to claim 10, wherein said personal hearing loss information for each respective hearing aid user is derived at a location remote from said facility.

* * * * *